(12) United States Patent
Denis et al.

(10) Patent No.: US 6,433,151 B1
(45) Date of Patent: Aug. 13, 2002

(54) ERYTHROMYCIN DERIVATIVES, A PROCESS FOR THEIR PREPARATION AND THEIR USE AS MEDICAMENTS

(75) Inventors: Alexis Denis; Giuseppe Gigliotti, both of Paris (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/350,224

(22) Filed: Jul. 8, 1999

(30) Foreign Application Priority Data

Jul. 9, 1998 (FR) .............................. 98 08795
Apr. 26, 1999 (FR) .............................. 99 05245

(51) Int. Cl.$^7$ .............................................. C07H 17/08
(52) U.S. Cl. ..................... 536/7.2; 536/7.3; 536/7.4; 514/29
(58) Field of Search .................. 514/29; 536/7.2–7.4

(56) References Cited

U.S. PATENT DOCUMENTS 5,527,780 A * 6/1996 Agouridas et al. ............ 514/29
5,635,485 A * 6/1997 Agouridas et al. ............ 514/29

FOREIGN PATENT DOCUMENTS

| WO | WO 9717356 | 5/1997 |
|----|------------|--------|
| WO | WO 9809978 | 3/1998 |

\* cited by examiner

Primary Examiner—James O. Wilson
Assistant Examiner—Howard V. Owens, Jr.
(74) Attorney, Agent, or Firm—Bierman, Muserlian and Lucas

(57) ABSTRACT

The invention relates to compounds of the formula (I)

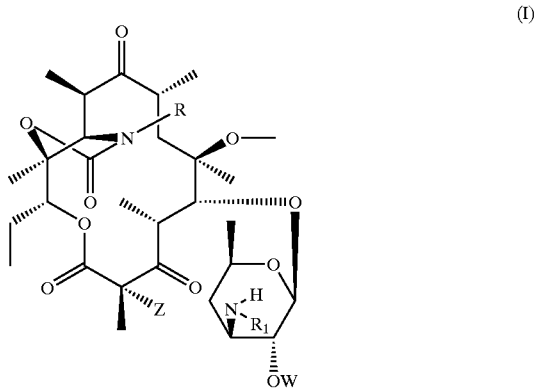

in which
R represents a radical $(CH_2)_m O_n(X)YAr$ in which m represents the number 0 or 1,
n represents the number 0 or 1,
X represents a radical $(NH)_a$, $CH_2$ or $SO_2$, where a represents the number 0 or 1,
Y represents a radical $(CH_2)_b$—$(CH=CH)_c$—$(CH_2)_d$, where c=0 or 1 and b+c+d ≦8,
Z represents a hydrogen or halogen atom,
Ar represents an optionally substituted aryl or heteroaryl radical and
W represents a hydrogen atom or an acyl radical, and their acid addition salts.

The compounds of the formula (1) have antibiotic properties.

11 Claims, No Drawings

ERYTHROMYCIN DERIVATIVES, A PROCESS FOR THEIR PREPARATION AND THEIR USE AS MEDICAMENTS

The present invention relates to new erythromycin derivatives, a process for their preparation and their use as medicaments.

The invention relates to compounds of the formula (I)

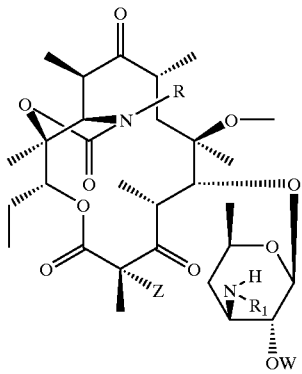

(I)

in which

R represents a radical $(CH_2)_m O_n(X)YAr$ in which m represents the number 0 or 1, n represents the number 0 or 1, X represents a radical $(NH)_a$, $CH_2$ or $SO_2$, where a represents the number 0 or 1, Y represents a radical $(CH_2)_b—(CH=CH)_c—(CH_2)_d$, where c=0 or 1 and b+c+d ≤8, Z represents a hydrogen or halogen atom, Ar represents an optionally substituted aryl or heteroaryl radical, $R_1$ represents a hydrogen atom or a methyl radical and W represents a hydrogen atom or an acyl radical, and their acid addition salts.

Acid addition salts which may be mentioned are the salts formed with acetic, propionic, trifluoroacetic, maleic, tartaric, methanesulphonic, benzenesulphonic or p-toluenesulphonic acid, and especially stearic, ethylsuccinic or laurysulphonic acid.

The aryl radical can be a phenyl or naphthyl radical. The substituted or unsubstituted heterocyclic radical can be the thienyl, furyl, pyrrolyl, thiazolyl, oxazolyl or imidazolyl radical, for example the 4-(3-pyridinyl)-1H-imidazolyl, thiadiazolyl, pyrazolyl or isopyrazolyl radical, a pyridyl, pyrimidyl, pyridazinyl or pyrazinyl radical, or an indolyl, benzofuranyl, benzothiazyl or quinolinyl radical.

These radicals can carry one or more groups chosen from the group consisting of hydroxyl radicals, halogen atoms, $NO_2$ radicals, C≡N radicals, alkyl, alkenyl or alkinyl, O-alkyl, O-alkenyl or O-alkinyl, S-alkyl, S-alkenyl or S-alkinyl and N-alkyl, N-alkenyl or N-alkinyl radicals containing up to 12 carbon atoms and optionally substituted by one or more halogen atoms, the radical,

$R_a$ and $R_b$ being identical or different and representing a hydrogen atom or an alkyl radical containing up to 12 carbon atoms, the radical

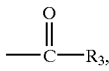

$R_3$ representing an alkyl radical containing up to 12 carbon atoms, or an optionally substituted aryl or heteroaryl radical, or carboxylic aryl, O-aryl or S-aryl or 5- or 6 -membered heterocyclic aryl, O-aryl or S-aryl radicals, containing one or more heteroatoms, optionally substituted by one or more of the substituents mentioned below. Preferred heterocyclic radicals which may be mentioned are, inter alia

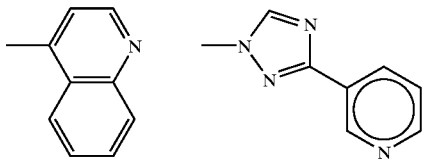

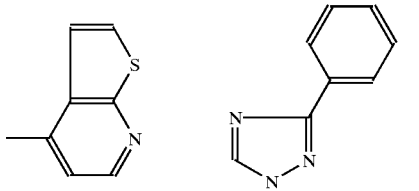

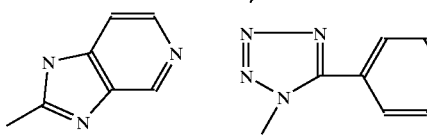

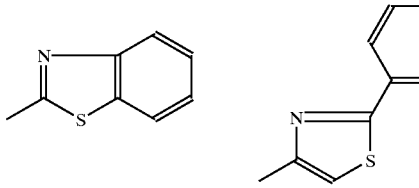

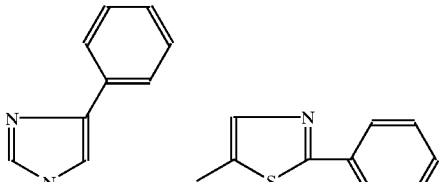

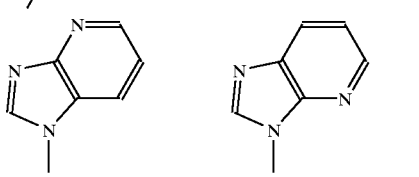

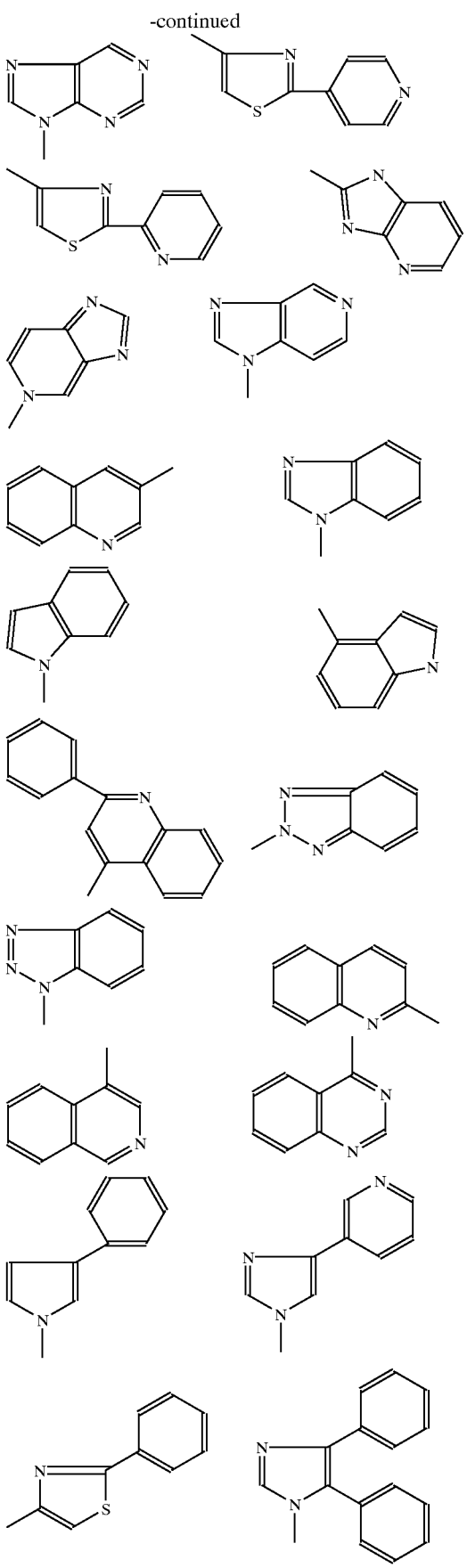

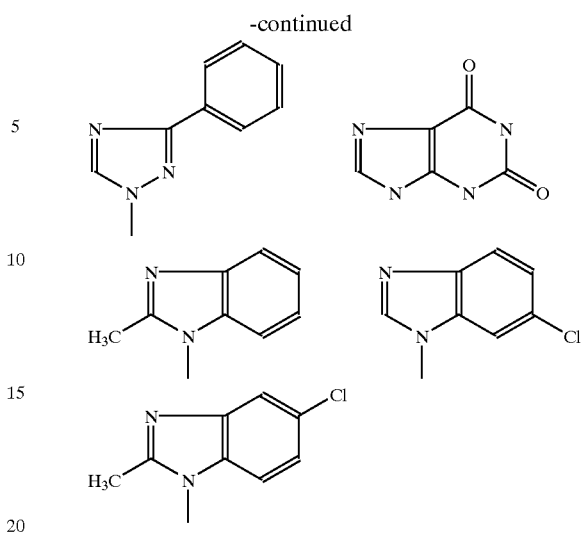

and the heteroyclic radicals considered in European Patent Applications 487411, 596802, 676409 and 680967. These preferred heterocyclic radicals can be substituted by one or more functional groups.

Halogen preferably represents a fluorine, chlorine or bromine atom.

The invention particularly relates to the compounds of the formula (I) in which Z represents a hydrogen atom, those in which W represents a hydrogen atom, those in which $R_1$ represents a methyl radical, and those in which X represents a $CH_2$ radical.

The invention more particularly relates to the compounds in which R represents a radical $(CH_2)_3Ar$, $(CH_2)_4Ar$ or $(CH_2)_5Ar$, Ar having its above meaning.

The invention especially relates to the compounds of the formula (I) in which Ar represents a radical:

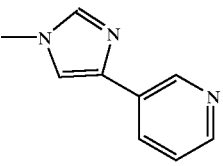

The invention very particularly relates to the compounds of the formula (I) of which the detailed preparation is given below in the experimental part.

The products of the general formula (I) have a very good antibiotic activity on Gram$^⊕$ bacteria, such as staphylococci, streptococci and pneumococci. The compounds of the invention can therefore be used as medicaments in the treatment of infections by sensitive germs, and in particular in that of staphylococcoses, such as staphylococcal septicaemias, malignant staphylococcoses of the face or skin, pyodermatitis, septic or suppurating wounds, furuncles, anthrax, phlegmons, erysipelas and acne, staphylococcoses, such as acute primary or post-influenzal anginas, bronchopneumonia and pulmonary suppuration, streptococcoses, such as acute anginas, otitis, sinusitis and scarlet fever, and pneumococcoses, such as pneumonia and bronchitis; brucellosis, diphtheria and gonococcosis.

The products of the present invention are also active against infections caused by germs such as Haemophilus influenzae, Moraxella catarrhalis, Rickettsiae, Mycoplasma pneumoniae, Chlamydia, Legionella, Ureaplasma, Toxoplasma or germs of the genus Mycobacterium.

As medicaments, and in particular antibiotic medicaments, the present invention thus also relates to the products of the formula (I) as defined above, and to their addition salts with pharmaceutically acceptable mineral or organic acids, As medicaments, and in particular antibiotic medicaments, the invention more particularly relates to the product of example 1 and the product of example 2 as well as their pharmaceutically acceptable salts.

The invention also relates to pharmaceutical compositions comprising at least one of the medicaments defined above as the active principle.

These compositions can be administered buccally, rectally or parenterally, or locally by topical application to the skin and mucous membranes, but the preferred administration route is the buccal route. They can be solid or liquid and can be in the pharmaceutical forms usually used in human medicine, such as, for example, simple or coated tablets, capsules, granules, suppositories, injectable preparations, ointments, creams and gels; they are prepared by the usual methods. The active principle or principles can be incorporated in them with the excipients conventionally employed in these pharmaceutical compositions, such as talc, gum arabic, lactose, starch, magnesium stearate, cacao butter, aqueous or non-aqueous vehicles, fatty substances of animal or plant origin, paraffin derivatives, glycols, various wetting, dispersing or emulsifying agents and preservatives.

These compositions can also be in the form of a powder for dissolving extemporaneously in a suitable vehicle, for example apyrogenic sterile water.

The dose administered can be varied according to the condition treated, the subject in question, the administration route and the product under consideration. It can be, for example, between 50 mg and 1,000 mg per day perorally, for example 300 to 900 mg in adults for the product of example 1.

The invention also relates to a process for the preparation of compounds of the formula (I), characterized in that a compound of the formula (II)

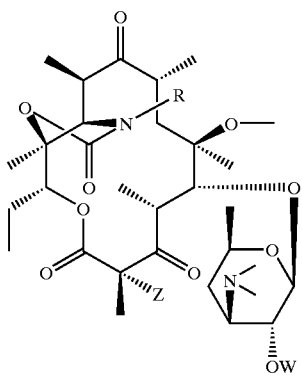

(II)

in which R, Z and W have their above meaning, is subjected to the action of a demethylating agent to obtain a mixture of corresponding compounds of the demethylated and didemethylated formula (I), which is separated to obtain the required compound of the formula I.

The demethylated and didemethylated compounds are separated by conventional processes, for example by chromatography. The compounds of the formula (II) used as the starting substances are described in particular in European Patents 0487411, 596802, 606024, 614905 and 680967. The demethylating agent which may be used is diethyl azodicarboxylate; or iodine in the presence of sodium acetate.

EXAMPLE 1

N-Demethyl-11,12-dideoxy-3-de[(2,6-dideoxy-3-C-methyl-3-O-methyl-alpha-L-ribohexopyranosyl)-oxy]-6-O-methyl-3-oxo-12,11-[oxycarbonyl[[4-[4-(3-pyridinyl)-1H-imidazol-1-yl]butyl]imino]]-erythromycin 10 g 11,12-dideoxy-3-de((2,6-dideoxy-3-C-methyl-3-O-methyl-alpha-L-ribohexopyranosyl)oxy)-6-O-methyl-3-oxo-12,11-(oxycarbonyl((4-(4-(3-pyridinyl)-1H-imidazol-1-yl)butyl)imino))-erythromycin are introduced into 150 cm$^3$ acetone. The reaction mixture is stirred until the solid has dissolved, and 3.83 cm$^3$ diethyl azodicarboxylate are introduced. Stirring is continued for 3 hours and the mixture is brought to dryness to give 14.48 g of the product, which is chromatographed over silica by eluting with a mixture of methylene chloride/methanol/ammonia (90-10-1). 3.16 g of the required crude product are obtained. After recrystallization from heptane, the required product is obtained.

HPLC titre 86%

| Microanalysis | C: 62.3% | theory 63.22% |
|---|---|---|
| | H: 8.1% | theory 7.96% |
| | N: 8.8% | theory 8.78% |

EXAMPLE 2

N-Demethyl-11,12-dideoxy-3-de((2,6-dideoxy-3-C-methyl-3-O-methyl-alpha-L-ribohexopyranosyl)oxy)-6-O-methyl-3-oxo-12,11-(oxycarbonyl(2-(3-(4-quinolinyl)-propyl)-hydrazono))-erythromycin By following the above procedure, starting from 11,12-dieoxy-3-de((2,6-dideoxy-3-C-methyl-3-O-methyl-alpha-L-ribohexopyranosyl)oxy)-6-O-methyl-3-oxo-12,11-(oxycarbonyl-(2-(3-(4-quinolinyl)propyl)hydrazono))-erythromycin, the required product was obtained.

EXAMPLE 3

N-Demethyl-11,12-dideoxy-3-de((2,6-dideoxy-3-C-methyl-3-O-methyl-alpha-L-ribohexopyranosyl)oxy)-6-O-methyl-3-oxo-12,11-(oxycarbonyl((4-phenylbutyl)imino))-erythromycin By following the procedure in example 1, starting from 11,12-dideoxy-3-de((2,6-dideoxy-3-C-methyl-3-O-methyl-alpha-L-ribohexopyranosyl)oxy)-6-O-methyl-3-oxo-12,11-(oxycarbonyl-((4-phenylbutyl)imino))-erythromycin, the required product was obtained.

rf=0.14 (isopropyl ether-methanol-triethylamine 80-10-10).

EXAMPLE 4

N-Didemethyl-11,12-dideoxy-3-de[(2,6-dideoxy-3-C-methyl-3-O-methyl-alpha-L-ribohexopyranosyl)oxy]-6-O-methyl-3-oxo-12,11-[oxycarbonyl[[4-[4-(3-pyridinyl)-1H-imidazol-1-yl]butyl]imino]]3-erythromycin 7.7 cm$^3$ diethyl azodicarboxylate are added at 20–25° C. to a solution containing 20 g 11,12-dideoxy-3-de((2,6-dideoxy-3-C-methyl-3-O-methyl-alpha-L-ribohexopyranosyl)oxy)-6-O-methyl-3-oxo-12,11-(oxycarbonyl-((4-(4-(3-pyridinyl)-1H-imidazol-1-yl)butyl)- imino))-erythromycin in 300 cm³ acetone. The mixture is stirred at 20–25° C. for 4 hours. It is brought to dryness. This gives 28.70 g product, which is chromatographed over silica by elution with a mixture of methylene chloride-methanol-ammonia 90-10-01. The first fraction is collected and is evaporated to dryness to give 14 g product, which is introduced into a mixture of 140 cm³ methanol and 70 cm³ 2N hydrochloric acid solution. The mixture is stirred for 24 hours. The pH is brought to 7 by addition of 20% ammonia. The mixture is extracted with methylene chloride. The aqueous phase is re-extracted with methylene chloride. The organic phases are dried with sodium sulphate. They are filtered, and the filtrate is brought to dryness. This gives 14.4 g product, which is chromatographed over silica. The column is eluted with a mixture of methylene chloride-methanol-ammonia 90-10-01. The expected crude product is collected and brought to dryness by distillation under reduced pressure. This gives 5.4 g of the required crude product, which is made into a paste in heptane. The product obtained is stirred for one hour at 2–25° C., washed, drained and dried. 4.5 g of the required product are obtained.

| Analysis | C 41 H 61 N5 O10 | |
|---|---|---|
| | Calculated | Found |
| C | 62.82 | 62.5 |
| H | 7.84 | 7.9 |
| N | 8.93 | 8.9 |

Examples of Pharmaceutical Compositions

Compositions comprising the following constituents are prepared:

| Product of example 1 | 300 mg |
|---|---|
| Excipient q.s.p | 1 g |

Details of the excipient: starch, talc, magnesium stearate

Pharmacological Study of the Products of the Invention

Method of Dilutions in a Liquid Medium

A series of tubes in which the same amount of sterile nutrient medium is distributed is prepared. Increasing amounts of the product to be studied are distributed in each tube, and each tube is then seeded with a strain of bacteria. After incubation for twenty-four hours in an oven at 37° C., the inhibition of growth is evaluated by transillumination, from which the minimum inhibitory concentrations (MIC), expressed in micrograms/cm³, can be determined.

The following results were obtained with the product from example 1 and from example 2 (reading taken after 24 hours).

| | | | Ex. 1 | Ex. 2 |
|---|---|---|---|---|
| S. aureus | 011UC4 | ery S | 0.300 | 0.080 |
| S. aureus | 011UC4 + serum 50% | ery S | 0.040 | 0.150 |
| S. aureus | 011B18c | oxa S ery R | | |

-continued

| | | | Ex. 1 | Ex. 2 |
|---|---|---|---|---|
| S. aureus | 011GR12c | oxa S ery R | | |
| S. aureus | 011GO25I | oxa S ery R | 5.000 | 0.600 |
| S. epidermidis | 012GO11I | oxa S ery R | 0.150 | 0.300 |
| S. aureus | 011CB20c | oxa R ery R | | |
| S. epidermidis | 012GO40c | oxa R ery R | | |
| S. pyogenes | 02A1UC1 | ery S | 0.800 | 0.040 |
| S. agalactiae | 02B1HT1 | ery S | <=0.02 | 0.020 |
| E. faecalis | 02D2UC1 | ery S | 0.080 | 0.040 |
| E. faecium | 02D3HT1 | Ery S | 0.080 | 0.040 |
| Streptococcus gr. G | 02GOGR5 | Ery S | 0.080 | 0.040 |
| S. mitis | 02MitCB1 | Ery S | 0.080 | <=0.01 |
| S. pyogenes | 02A1SJc | ery R | | |
| S. agalactiae | 02B1SJ1c | ery R | 0.600 | 0.150 |
| E. faecalis | 02D2DU15c | ery R | >40 | >20 |
| Streptococcus gr. G | 02GOgr4c | ery R | | |
| S. sanguis | 02SgGr10I | ery R | 0.150 | 0.150 |
| S. mitis | 02MitGR16I | ery R | 0.080 | 0.080 |
| S. pneumoniae | 032UC1 | ery S | <=0.02 | <=0.01 |
| S. pneumoniae | 030GR20 | ery S | <=0.02 | <=0.01 |
| S. pneumoniae | 030SJ51 | ery R | 0.080 | 0.080 |
| S. pneumoniae | 030CR18c | ery R | 10.000 | 2.500 |
| S. pneumoniae | 030PW23c | ery R | 0.150 | 0.080 |
| S. pneumoniae | 030R01I | ery R | 0.150 | 0.300 |
| S. pneumoniae | 030SJ1c | ery R | 0.080 | 0.150 |

What is claimed is:
1. A compound selected from the group consisting of a compound of the formula

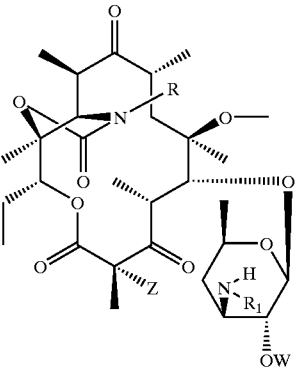

I wherein R is $-(CH_2)_mO_n(X)-Y-Ar$, m is 0 or 1, n is 0 or 1, X is selected from the group $-(NH)_a-$, $-CH_2-$ and $-SO_2-$, a is 0 or 1, Y is $-(CH_2)_b-(CH=CH)_c$ $-(CH_2)_d-$, c is 0 or 1, b+c+d≦8, Z is hydrogen or halogen, Ar is aryl or heteroaryl unsubstituted or substituted with at least one member of the group consisting of a) —OH, halogen, $-NO_2$, —CN and b) alkyl, alkenyl, alkynyl, alkoxy, alkynloxy, alkynyloxy, alkylthio, alkenylthio, alkynylthio, N-alkyl, N-alkenyl and N-alkynyl, all up to 12 carbon atoms and optionally substituted by at least one halogen,

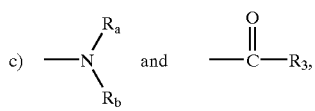

$R_a$ and $R_b$ are individually hydrogen or alkyl of 1 to 12 carbon atoms, $R_3$ is selected from the group consisting of alkyl of 1 to 12 carbon atoms, optionally substituted aryl and heteroaryl, $R_1$ is hydrogen or methyl, W is hydrogen or acyl of an organic carboxylic acid and its non-toxic, pharmaceutically acceptable acid addition salts.

2. A compound of claim 1 wherein Z is hydrogen.
3. A compound of claim 1 wherein W is hydrogen.
4. A compound of claim 1 wherein $R_1$ is methyl.
5. A compound of claim 1 wherein X is —$CH_c$—.
6. A compound of claim 1 wherein R is selected from the group consisting of —$(CH_2)_3$—Ar, —$(CH_2)_4$—Ar and —$(CH_2)_5$—Ar wherein Ar is defined as in claim 1.
7. A compound of claim 1 wherein Ar is

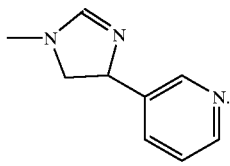

8. A compound of claim 1 selected from the group consisting of

N-demethyl-11,12-dideoxy-3-de[(2,6-dideoxy-3-C-methyl-3-O-methyl-.alpha.-L-ribo-hexopyranosyl)oxy]-6-O-methyl-3-oxo-12,11-[oxycarbonyl [[4-[4-(3-pyridinyl) -1H-imidazol-1-yl]butyl]imino]]-erythromycin, N-dimethyl-11,12-dideoxy-3-de((2,6-dideoxy-3-C-methyl-3-O-methyl-alpha-L-ribohexopyranosyl)oxy)-6-O-methyl-3-oxo-12,11-(oxycarbonyl(2-(3-(4-quinolynyl)propyl)hydrazono))-erythromycin and N-didemethyl-11,12-dideoxy-3-de[(2,6-dideoxy-3-C-methyl-3-O-methyl-alpha-L-ribohexopyranosyl)oxy]-6-O-methyl-3-oxo-12-11-[oxycarbonyl[[4-[4-(3-pyridinyl)-1H-imidazol-1-yl]butyl]imino]]-erythromycin.

9. An anti-bacterial composition comprising an antibacterially effective amount of a compound of claim 1 and an inert pharmaceutical carrier.

10. An anti-bacterial composition comprising an antibacterially effective amount of a compound of claim 8 and an inert pharmaceutical carrier.

11. A method of treating bacterial infections in warm-blooded animals comprising administering to warm-blooded animals an antibacterially effective amount of a compound of claim 1.

* * * * *